(12) United States Patent
Batzer

(10) Patent No.: US 10,426,406 B2
(45) Date of Patent: Oct. 1, 2019

(54) DETECTING AND SUPPRESSING NOISE SIGNALS OF A DIFFERENTIAL VOLTAGE MEASURING SYSTEM

(71) Applicant: Ulrich Batzer, Buckenhof (DE)

(72) Inventor: Ulrich Batzer, Buckenhof (DE)

(73) Assignee: Siemens Healthcare GmbH, Erlangen (DE)

( * ) Notice: Subject to any disclaimer, the term of this patent is extended or adjusted under 35 U.S.C. 154(b) by 64 days.

(21) Appl. No.: 15/785,637

(22) Filed: Oct. 17, 2017

(65) Prior Publication Data

US 2018/0103907 A1 Apr. 19, 2018

(30) Foreign Application Priority Data

Oct. 19, 2016 (DE) .................. 10 2016 220 473

(51) Int. Cl.
*A61B 5/00* (2006.01)
*A61B 5/0245* (2006.01)
(Continued)

(52) U.S. Cl.
CPC .......... *A61B 5/7217* (2013.01); *A61B 5/0245* (2013.01); *A61B 5/0428* (2013.01); *A61B 5/0432* (2013.01); *A61B 5/04286* (2013.01); *A61B 5/04525* (2013.01); *A61B 5/6844* (2013.01); *A61B 5/7203* (2013.01);
(Continued)

(58) Field of Classification Search
CPC . A61B 5/0245; A61B 5/0428; A61B 5/04286; A61B 5/0432; A61B 5/04525; A61B 5/6844; A61B 5/7203; A61B 5/7217; A61B 5/7267; A61B 5/7285; A61N 5/1068
See application file for complete search history.

(56) References Cited

U.S. PATENT DOCUMENTS 5,987,348 A  11/1999 Fischer et al.
9,151,810 B2  10/2015 Demharter et al.
(Continued)

FOREIGN PATENT DOCUMENTS

DE  69828372 T2  12/2005
DE  102006053613 A1  5/2008

OTHER PUBLICATIONS

German Office Action for German Application No. 102016220473.4, dated May 15, 2017.
(Continued)

*Primary Examiner* — George Manuel
(74) *Attorney, Agent, or Firm* — Lempia Summerfield Katz LLC

(57) ABSTRACT

Methods, noise detection devices, and differential voltage measuring systems are provided for detecting noise signals for the purpose of measuring cardiac movements in a patient. In the method, contact is made with the patient by at least two measuring electrodes having at least one associated measuring channel. Furthermore, a heartbeat measurement is performed. During the heartbeat measurement, signals from the patient are detected over the at least one measuring channel. Then, a check is made of whether the detected signals have been caused by noise by comparing the detected signals with at least one heartbeat type that was identified in the course of the learning procedure.

13 Claims, 4 Drawing Sheets

(51) Int. Cl.
*A61B 5/0428* (2006.01)
*A61B 5/0432* (2006.01)
*A61B 5/0452* (2006.01)
*A61N 5/10* (2006.01)

(52) U.S. Cl.
CPC .......... *A61B 5/7267* (2013.01); *A61B 5/7285* (2013.01); *A61N 5/1068* (2013.01)

(56) References Cited

U.S. PATENT DOCUMENTS

| | | | |
|---|---|---|---|
| 2003/0220578 A1* | 11/2003 | Ho | A61B 5/0263 600/521 |
| 2008/0114237 A1 | 5/2008 | Demharter et al. | |
| 2016/0095521 A1* | 4/2016 | Inan | A61B 5/7207 600/301 |

OTHER PUBLICATIONS

Meziane, N., et al. "Dry electrodes for electrocardiography." Physiological measurement 34.9 (Aug. 2013): R47.

* cited by examiner

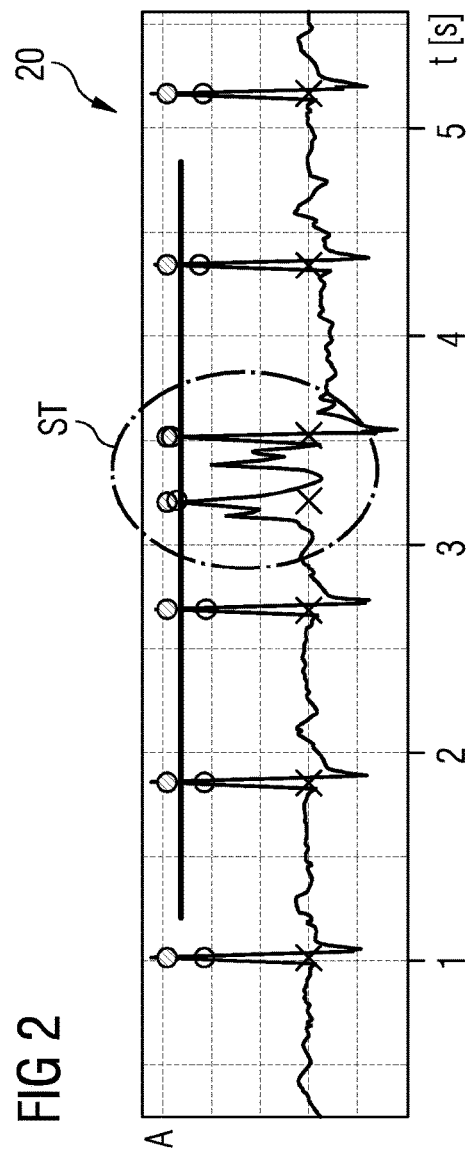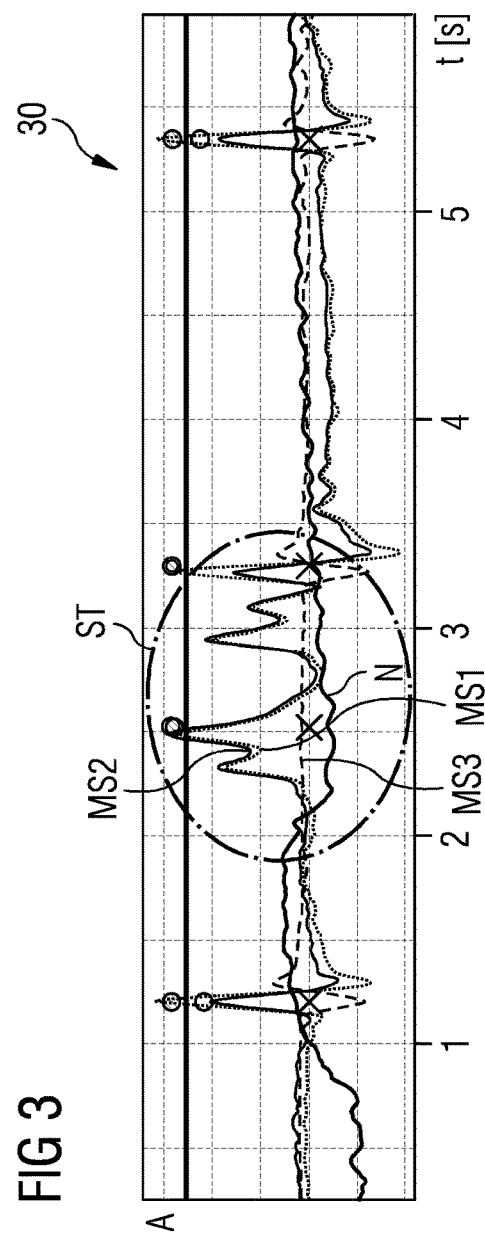

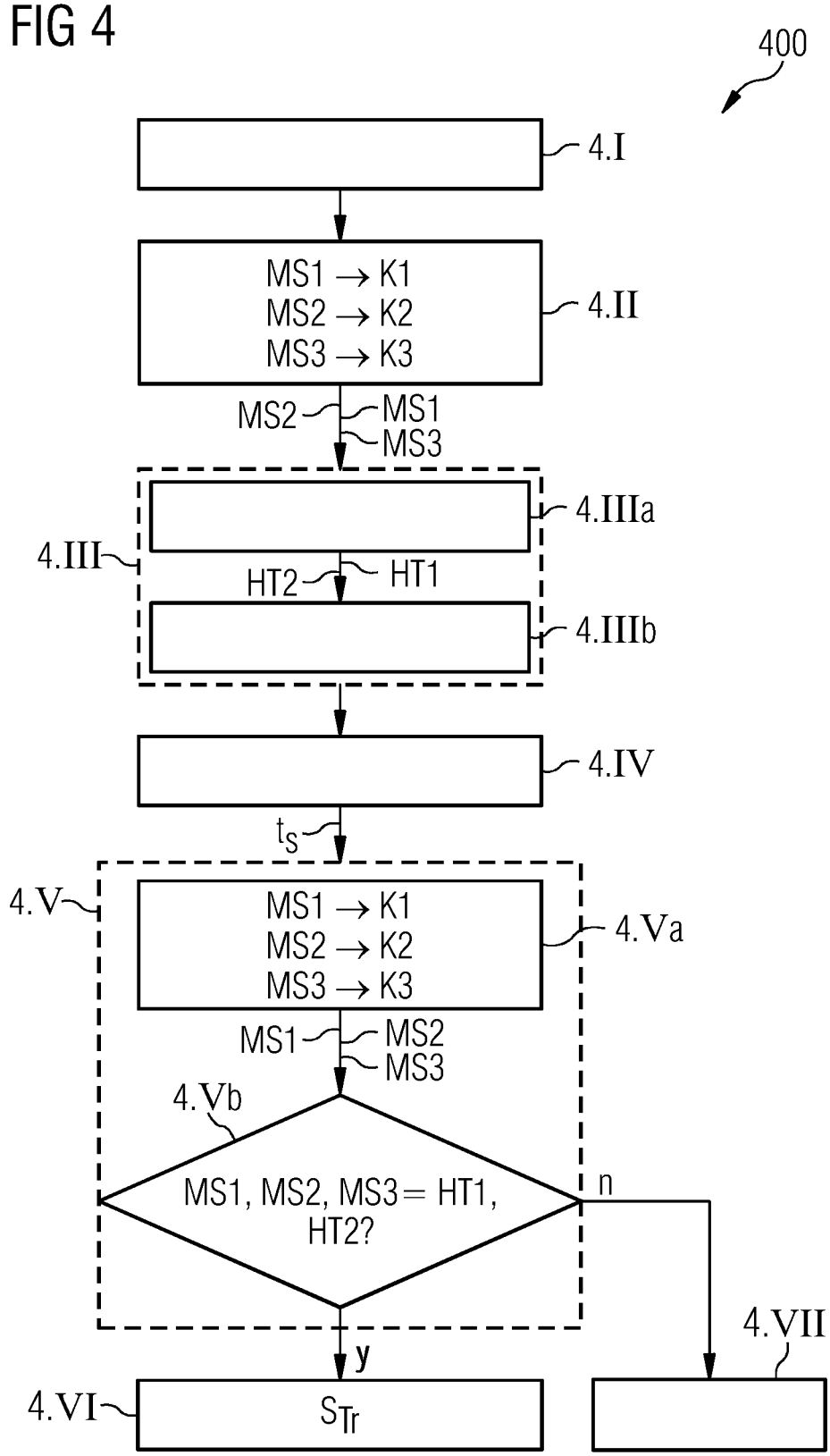

DETECTING AND SUPPRESSING NOISE SIGNALS OF A DIFFERENTIAL VOLTAGE MEASURING SYSTEM

The applications claims the benefit of German Patent Application No. Del. 10 2016 220 473.4, filed Oct. 19, 2016, incorporated by reference in its entirety.

TECHNICAL FIELD

The disclosure relates to a method for detecting noise signals of a differential voltage measuring system. The disclosure further relates to a noise detection device. Moreover, the disclosure relates to a differential voltage measuring system.

BACKGROUND

Electrocardiogram (ECG) measuring devices are primarily used for measuring and monitoring the cardiac function of a patient, and for this purpose the total electrical activity of all the heart muscle fibers is recorded, e.g., by way of at least two measuring electrodes, as a so-called ECG signal. In addition to the two measuring electrodes, a third electrode is conventionally used for potential equalization. This electrode is also called a right leg drive (RLD) electrode.

When differential physiological signals, such as ECG signals, are measured, various types of noise occur. A very frequent type of noise is common mode noise. This noise arises when noise signals are transmitted through the patient to the two measuring inputs and dissimilar conditions, such as different impedances and capacitances, occur at the measuring inputs, with the result that the noise signals are not suppressed.

Another type of noise is electrode-based noise, that is to say noise that does not pass through the patient like common mode noise but is produced by spontaneous changes at the boundary between the electrode and the skin.

The electrode-based noise that most frequently occurs in an ECG is produced by pressure on the electrode or by tension on a cable connected to the electrode. These procedures alter the spacing between the electrode and the skin, so that the electrical properties of the boundary between the electrode and the skin change too.

Moreover, noise may pass through as a result of ionization of an electrode. This phenomenon occurs, for example, when X-rays are used for the purpose of medical imaging or therapy.

One way of reducing noise resulting from ionization consists in reducing the resistance at the boundary between the electrode and the skin. If the boundary has small resistance values, the ionization will not have a major effect. For this reason, conventionally the attempt is made to optimize the boundary between the electrode and the skin appropriately. However, this is not always possible in all cases.

Moreover, there are methods for monitoring the measured signals by a so-called single-channel heartbeat recognition algorithm. However, even with this algorithm noise may not always be distinguished from irregular heartbeats, which occur particularly frequently in patients suffering from heart disease.

SUMMARY AND DESCRIPTION

It is thus an object of the present disclosure to develop a method and a device for detecting noise signals in a differential measuring system that are suitable, even in patients for whom the underlying measured signal is very irregular, for distinguishing noise from a measured signal of this kind.

The scope of the present disclosure is defined solely by the appended claims and is not affected to any degree by the statements within this summary. The present embodiments may obviate one or more of the drawbacks or limitations in the related art.

This object is achieved by a method for detecting noise signals of a differential voltage measuring system, by a noise detection device, and by a differential voltage measuring system.

In the method for detecting electrode-based noise signals of a differential voltage measuring system, (e.g., an ECG measuring system), for measuring cardiac movements in a patient, contact is made with the patient by at least two measuring electrodes having at least one associated measuring channel. In this context, the term "patient" may refer to a person or an animal to be investigated having a blood circulation with a heart. In this context, the term "electrode-based" may refer to the noise signal in question results from a change in the region where the electrodes are in contact with the patient's skin. As mentioned above, a change of this kind may be based on mechanical interference or an interaction with ionizing radiation. In the context of the method, a heartbeat is measured, during which signals from the patient are detected over the at least one measuring channel and are checked to establish whether a detected signal has been caused by noise.

The check is performed by comparing the detected signals with at least one heartbeat type that was identified in the course of a learning procedure. The learning procedure may be performed in advance, e.g., before the actual measurement of the patient's heartbeat is carried out. With the aid of the learning procedure, patterns of heartbeat types that occur in a particular patient to be investigated are detected. Advantageously, the learning procedure is performed with no noise, that is to say that the noise to be expected during the actual measuring procedure is deliberately eliminated. For example, noise may be caused by the influence of X-rays or mechanical forces. By eliminating or suppressing the expected noise during the learning procedure, only signals that correspond to a heartbeat type that occurs in the respective patient are detected during the learning procedure. In this context, in particular in the case of patients with arrhythmia, signals may occur that may conventionally easily be confused with noise signals during the actual heartbeat measurement.

Advantageously, in the case of the method, an arrhythmic heartbeat signal of this kind is associated with a particular heartbeat type in the course of a learning procedure, and may then be recognized again during the actual heartbeat measurement. Consequently, recognition of a heartbeat during the actual heartbeat measurement, during which noise attributable to external sources of noise such as X-rays or external mechanical influence also occurs, may be performed more reliably. As a result of the learning procedure, individual characteristic heartbeat patterns of a patient may be identified in advance and recognized again during the actual heartbeat measurement. For example, up to ten different heartbeat types may occur in an individual patient. Advantageously, recognition of the heartbeat is therefore configured to the individual patient so that the reliability and accuracy of this procedure is enhanced.

The noise detection device has an input interface for detecting signals from a patient over at least one measuring channel, e.g., at least two measuring channels. Moreover, the noise detection device also includes a heartbeat checking unit for the purpose of checking whether a detected signal has been caused by noise. The heartbeat checking unit is intended to compare the detected signals with at least one heartbeat type of the patient that was identified in the course of a learning procedure. If the heartbeat checking unit establishes that a measured signal corresponds to a known heartbeat type, this measured signal is classified as an underlying measured signal. If, by contrast, it is established that the measured signal does not correspond to any of the stored heartbeat types, the measured signal is classified as noise.

The differential voltage measuring system has at least two measuring electrodes. Moreover, the differential voltage measuring system includes a measuring device that includes at least one measuring channel for detecting measured signals of the at least two measuring electrodes. Furthermore, the differential voltage measuring system has a noise detection device.

Certain components of the differential voltage measuring system may take the form of software components. This is true, in particular, of parts of the noise detection device, such as the heartbeat checking unit. In principle, however, the heartbeat checking unit may also be constructed in part, in particular, if particularly fast processing is required, as software-supported hardware such as FPGAs or similar. Similarly, the required interfaces may take the form of software interfaces, for example where data has only to be transferred from other software components. However, they may also take the form of interfaces that are constructed from hardware and are controlled by suitable software.

A construction largely in the form of software has the advantage that differential voltage measuring systems that have already been used hitherto may also be retrofitted in a simple manner by a software update in order to operate in the manner. To this extent, the object is also achieved by a corresponding computer program product having a computer program that may be loaded directly to a memory device of a differential voltage measuring system, having program sections in order to perform all the acts of the method when the program is run in the differential voltage measuring system. A computer program product of this kind may, in addition to the computer program, where appropriate include additional constituents such as documentation and/or additional components, including hardware components, such as hardware keys (e.g., dongles, etc.) for utilization of the software.

For the purpose of transport to the differential voltage measuring system and/or storage at or in the differential voltage measuring system there may serve a computer-readable medium, (e.g., a memory stick), a fixed disk, or another kind of transportable or permanently installed data medium, on which the program sections of the computer program that may be read in and run by a processor unit of the differential voltage measuring system are stored. The processor unit may have one or more cooperating microprocessors or similar.

In a particularly practical embodiment of the method, contact is made with the patient by three measuring electrodes, and the signals from the patient are detected over at least two measuring channels. Two measuring electrodes are associated with each measuring channel, with the result that the measuring channel receives a signal indicating the difference between the two measuring electrodes. In the case of three measuring electrodes, either the signal of a third measuring channel may be calculated from the signals of the at least two measuring channels with the aid of Kirchhoff's current law, or a third measuring channel, by which a third difference signal is measured, is directly provided.

When three measuring electrodes are used with two or three measuring channels, it may occur that heartbeat signals are also only detected over a single channel, while no such signal occurs over the other channels. Conventionally, in the course of a heartbeat measurement, a signal of this kind would be identified as noise. Advantageously, with the method, an arrhythmic heartbeat signal of this kind is now associated with a particular heartbeat type and may then be recognized again during the actual heartbeat measurement. Consequently, it is possible to recognize a heartbeat more reliably during the actual heartbeat measurement, even when noise attributable to external noise sources such as X-rays or external mechanical influences occurs at the same time.

In one embodiment of the method, signals from the patient are detected over the at least one measuring channel in the course of the learning procedure. Then, at least one heartbeat type is identified on the basis of the detected signals. The at least one identified heartbeat type is moreover stored in order to be used as a basis for comparison in the course of a subsequent heartbeat measurement. Advantageously, the learning procedure is performed without the source of noise connected up. This absence of noise may be achieved by disconnecting or screening any sources of noise. In this way, it is guaranteed that no noise signals are classified as heartbeat signals during the learning procedure. Consequently, the heartbeat types identified during the learning procedure are rated as reliable and correct.

In one embodiment of the method, during the learning procedure, characteristic features are identified during identification of the heartbeat type, on the basis of the detected signals, and the heartbeat type is stored together with the characteristic features associated with this heartbeat type. The characteristic features relate, for example, to the shape of the recorded measured curves of the signals, and may have particular variable values that characterize the detected measured signals more precisely.

In a particularly effective variant of the method, the characteristic features include at least one of the following variables: amplitude of a heartbeat, duration of a heartbeat, and the relationship between the amplitudes of the signals of different measuring channels.

The variable values may be utilized during the actual heartbeat measurement to compare the identified heartbeat types with the detected measured signals.

In a particular embodiment of the method, during the learning procedure, when characteristic features occur for the first time, a new heartbeat type is defined on the basis of the characteristic features. Characteristic features are associated with the respective heartbeat type and stored therewith. Subsequent signals having similar characteristic features are associated with the stored heartbeat type. That is to say that an additional heartbeat type is not stored for these signals.

There may be used, as examples of "similar" characteristic features, values or tolerances of in each case +/−33% of the total amplitude and edge steepness of the measured curve of an already identified heartbeat type in order to associate a heartbeat with an already identified heartbeat type, wherein this value is checked against the average value from the multi-channel measurement. Thus, if in the case of a three-channel measurement one channel agrees to within a few percent, the other two may have a greater deviation.

For example, a first heartbeat type may be stored for the underlying heartbeat of the patient and, in the case of arrhythmia, further heartbeat types may additionally be stored that have characteristic features differing from the first heartbeat type.

In the case of patients suffering from heart disease, up to ten different heartbeat types may be identified.

In a particularly frequent application of the method, a source of noise is connected up when the heartbeat is measured. To be more precise, the source of noise is switched on during measurement of the heartbeat. The source of noise may be a radiation source with ionizing radiation. When the heartbeat is measured, a signal is identified as the underlying signal if the signal may be associated with one of the stored heartbeat types. The signal is identified as noise if the signal cannot be associated with any of the stored heartbeat types. Advantageously, the source of noise is only connected up at the time of the actual heartbeat measurement, whereas it remains disconnected during a training phase or learning phase that is carried out in advance. Consequently, the heartbeat types identified in the learning phase are reliable and may serve for a comparison with the measured signals detected during the heartbeat measurement.

In a particularly practical embodiment of the method, if the signal has been identified as the underlying one, it is used as the trigger signal for an irradiation procedure. For example, an imaging procedure is synchronized with the cardiac movement with the aid of the trigger signal. If an X-ray imaging method is used for the imaging, noise signals may arise as a result of the X-rays emitted during this. If these noise signals are not recognized reliably, as is the case in a conventional procedure, then erroneous synchronization and hence either a deterioration in image quality or a time delay in image capture may result. Advantageously, these disadvantages are avoided as a result of improved noise signal recognition.

In a particularly effective embodiment of the method, during the heartbeat measurement properties of the boundary between the electrode and the skin are additionally measured, and noise or noise signals are additionally identified in dependence on measured values of the properties of the boundary between the electrode and the skin. In this embodiment, the boundary regions between the measuring electrodes and the patient's skin are thus additionally monitored directly, and the monitoring data is included in the decision on whether a measured signal is a noise signal or a signal of a patient's heartbeat, so the reliability of detecting noise signals is improved yet further.

BRIEF DESCRIPTION OF THE DRAWINGS

The disclosure will be explained again in more detail below with reference to the attached figures and on the basis of exemplary embodiments. Here, like components are provided with identical reference numerals in the various figures. In the figures:

FIG. 2 depicts an example of an electrocardiogram having an electrode-based noise signal that has been caused by ionizing radiation.

FIG. 3 depicts an example of an electrocardiogram that displays signals from three different measuring channels at the same time.

FIG. 4 depicts a flow diagram that represents a method for detecting electrode-based noise signals according to an exemplary embodiment.

DETAILED DESCRIPTION

Figure 1:
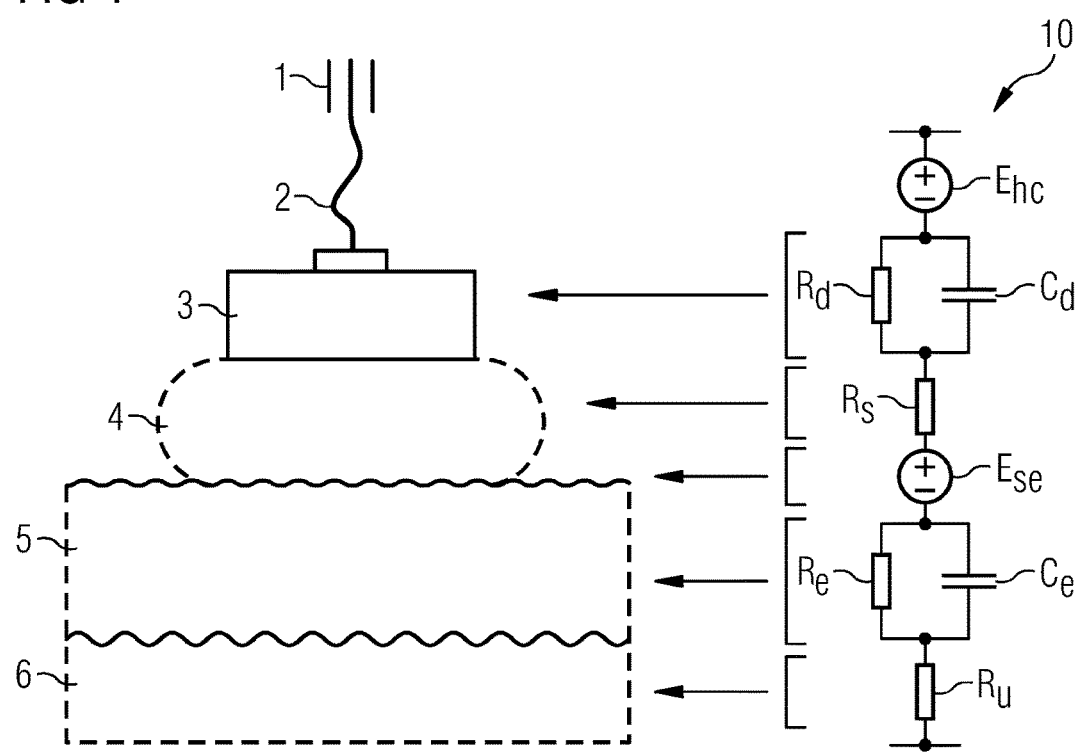
FIG. 1 depicts a schematic representation of an electrical model of a boundary between the electrode and the skin.

FIG. 1 depicts a representation 10, intended as a model of a boundary between an electrode and the skin. On the left-hand side of the representation 10, individual components of a boundary between the electrode and the skin are sketched, and the right-hand side of the representation 10 shows the circuit elements each corresponding to the individual components in the model, wherein circuit elements or groups of circuit elements corresponding to the individual components are connected to one another in series. An electrode 3 is electrically connected, by way of a shield 1 and a cable connection 2, to a measuring device, also called an ECG component (see FIG. 5). The electrode 3 is in contact with the skin of a patient by way of a gel 4. The skin includes an epidermis 5 to which the gel 4 is applied, and a layer 6 that lies below the epidermis 5 and includes the dermis and subcutaneous tissue.

The cable connection 2 between the electrode 3 and the shield 1 is modeled by a first voltage source $E_{hc}$. The electrode 3 itself is shown as a first parallel arrangement, connected in series to the first voltage source $E_{hc}$, including an ohmic resistor $R_d$ and a capacitor $C_d$. The gel 4 includes a first ohmic resistor $R_s$, and the boundary between the gel 4 and the epidermis is modeled by a second voltage source $E_{se}$. The epidermis 5 itself is shown as a second parallel arrangement including an ohmic resistor $R_e$ and a capacitor $C_e$. The region 6 lying below this and including the dermis and the subcutaneous tissue is shown as a second ohmic resistor $R_u$.

The electrode-based noise that occurs most frequently during an ECG measurement is produced by pressure on the electrode 3 or tension on the cable 2 connected to the electrode 3. This procedure changes the spacing between the electrode 3 and the skin 5, so the electrical properties in this region are also changed.

Ionization of the electrode 3, produced for example by X-rays, may also cause a significant amount of noise to pass through. In this case the electrical voltage produced, which is generated by the second voltage source $E_{se}$ that models the boundary between the gel 4 and the epidermis 5, is changed, that is to say that an additional voltage shift is produced between the gel 4 and the epidermis 5.

FIG. 2 represents an example of noise passing through with the aid of an ECG signal graph 20. In the ECG signal graph 20, the amplitude A of an ECG signal is shown over time t in seconds. As can be seen from FIG. 2, after the third heartbeat a noise signal ST occurs for a period of around 0.5 s, and this has the same amplitude and a similar signal shape to the heartbeats.

FIG. 3 depicts an ECG signal graph 30 that represents measured signals MS1, MS2, MS3 of three different channels or three different electrodes. Here, once again the amplitude A of the measured signals MS1, MS2, MS3 is shown over time t. A fourth signal is also shown, the noise level N of the first channel, that is to say the channel associated with the first measured signal MS1. During a noise ST, two channels (e.g., those associated with the measured signals MS1, MS2) have approximately the same measured signal curve, while a third channel (e.g., corresponding to the measured signal MS3) remains completely unaffected. In contrast, all the measuring channels display marked deflections on a heartbeat. However, unlike the situation shown in FIG. 3, this is not always the case in the same way. In the case of arrhythmic heartbeats, the mapping of the heart activity onto the measuring channels changes and, on individual measuring channels, may even almost disappear, so a signal of this kind would conventionally easily be interpreted as noise.

FIG. 4 depicts a flow diagram 400 by which a method for detecting electrode-based noise signals of a differential voltage measuring system for measuring cardiac movements of a patient is represented according to an exemplary embodiment.

In act 4.I, contact is made between the body of a patient P (see also FIG. 5) and three measuring electrodes E1, E2, E2, wherein the difference signals of in each case two measuring electrodes are each associated with a different measuring channel K1, K2, K3. Then, in act 4.II, measured signals MS1, MS2, MS3 are detected over three measuring channels K1, K2, K3 of the differential voltage measuring system. On the basis of the detected measured signals MS1, MS2, MS3, before the actual heart investigation, which in this exemplary embodiment serves to provide clocking for a CT imaging process, a learning procedure is carried out, corresponding to act 4.III. In act 4.IIIa, heartbeat types HT1, HT2 and their characteristic features are identified using measured signals MS1, MS2, MS3 that are unaffected by noise.

The characteristic features of the heartbeat types HT1, HT2 include for example the amplitude A of the measured signals MS1, MS2, MS3, the duration T of a signal of this kind, and the mapping of the heartbeat signals MS1, MS2, MS3 of the individual measuring channels K1, K2, K3 onto one another. In this case, the term "mapping" refers to the function of transposing the measured signals MS1, MS2, MS3 of the individual channels K1, K2, K3. In simplified terms, the mapping may be represented by the relationship between the amplitudes A of the heartbeat signals MS1, MS2, MS3 of the different channels K1, K2, K3. In act 4.IIIb, the recognized characteristic features of the measured signals MS1, MS2, MS3 are stored the first time they occur, as a new heartbeat type HT1, HT2, and subsequent heartbeat signals MS1, MS2, MS3 are associated with the same heartbeat type HT1, HT2 if they have similar characteristic features. In the simplest case, the memory includes only one heartbeat type HT1, if the heartbeats are regular and always the same. If arrhythmia occurs, correspondingly more heartbeat types HT1, HT2 are stored.

In act 4.IV, the differential voltage measuring system is alerted to the fact that CT imaging, during which the patient is irradiated by X-rays, will be started at a start time $t_S$.

In act 4.V, starting at the start time $t_S$, the actual investigation of the heart is performed, during which the detected heartbeats are to serve to trigger or synchronize the cardiac movement with CT imaging. First of all, in act 4.Va, measured signals MS1, MS2, MS3 from the patient P are detected. Then, in act 4.Vb, a check is carried out of whether the detected measured signals MS1, MS2, MS3 were caused by noise. For this purpose, the detected measured signals MS1, MS2, MS3 are compared with the heartbeat types HT1, HT2 identified and stored in the course of the learning procedure, and their characteristic features. If the comparison establishes that at least one of the measured signals MS1 MS2, MS3 that are detected simultaneously over the different channels K1, K2, K3 corresponds to one of the heartbeat types HT1, HT2 identified in the learning phase—which is characterized by "y" in FIG. 4—then the measured signals MS1, MS2, MS3 that are detected simultaneously are interpreted as heartbeat signals, and a corresponding trigger signal $S_{Tr}$ for controlling the CT imaging is generated in act 4.VI. If no agreement or similarity may be established between at least one of the simultaneously detected measured signals MS1, MS2, MS3 and one of the identified heartbeat types HT1, HT2—characterized by "n" in FIG. 4—then the simultaneously detected heartbeat signals MS1, MS2, MS3 are interpreted as noise, and no trigger signal $S_{Tr}$, which is intended to signal the occurrence of a heartbeat, is triggered in act 4.VII. Acts 4.V to 4.VII are repeated until the CT imaging finishes.

Figure 5:
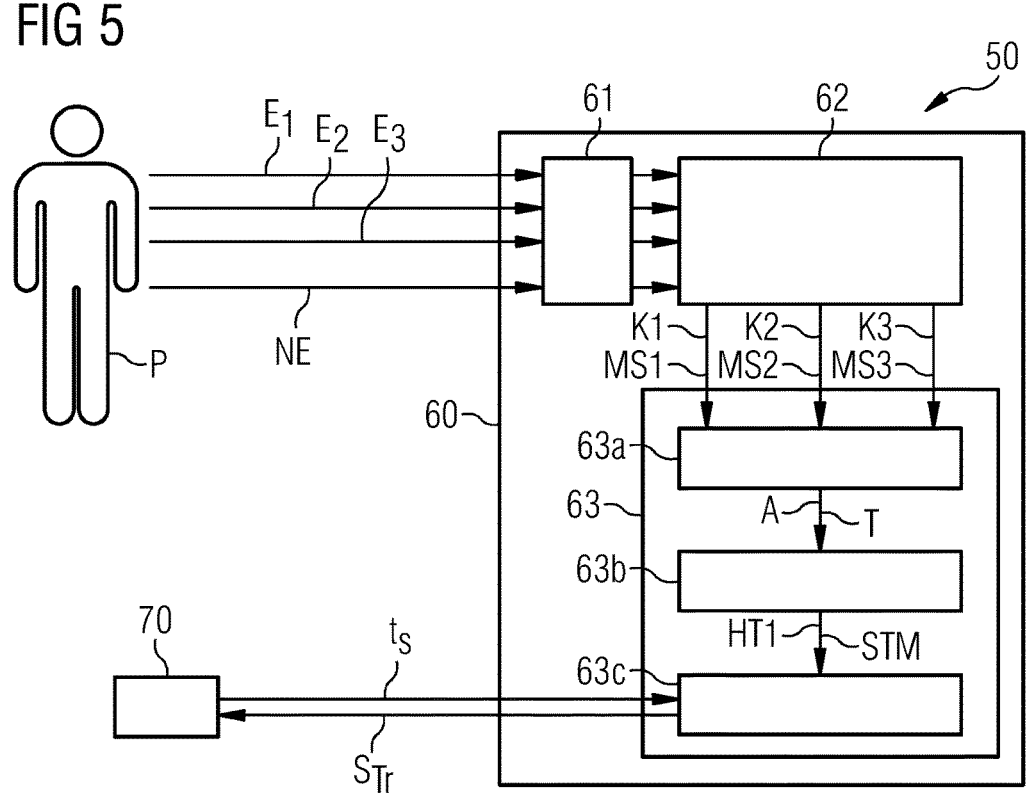
FIG. 5 depicts a block diagram that represents a detection device for detecting an electrode-based noise signal according to an exemplary embodiment.

FIG. 5 illustrates a schematic representation of a differential voltage measuring system 50 according to an exemplary embodiment. The differential voltage measuring system 50 includes three measuring electrodes E1, E2, E3 and a neutral electrode NE, each of which is in electrical contact with the body of a patient P to be investigated. Measured signals are detected from each of the measuring electrodes E1, E2, E3 and are passed on to an ECG component 60. The ECG component 60 serves to evaluate the detected measured signals and to generate a trigger signal $S_{Tr}$ that is transmitted to a CT system 70 in order to synchronize imaging with the heartbeat of the patient P. The ECG component 60 includes an analog input interface 61 that has for example an electromagnetic compatibility (EMC) protection function. An A/D converter 62 is electrically connected to the input interface 61 by way of a total of four channels. The detected measured signals and the signal from the neutral electrode NE are digitalized in the A/D converter 62. Three difference signals MS1, MS2, MS3 are identified from the measured signals and are passed on to a noise detection device 63 by way of three digital channels K1, K2, K3.

The noise detection device 63 has a multi-channel feature recognition unit 63a, which identifies features, such as the signal amplitude A and the duration T, of the detected measured signals and the difference signals MS1, MS2, MS3 corresponding thereto. The identified features A, T are then sent to a heartbeat checking unit 63b, which compares the identified features A, T with the corresponding characteristic features of stored heartbeat types HT1, HT2. If the identified features correspond to one of the stored heartbeat types HT1, HT2, the identified heartbeat type HT1 is transmitted to a trigger decision unit 63c. If no stored heartbeat type HT1, HT2 may be identified, a noise alert STM is sent to the trigger decision unit 63c. The trigger decision unit 63c uses the received signals as a basis to decide whether a trigger signal is to be transmitted to the CT system 70 or not. If the trigger decision unit 63c has received an alert that a heartbeat type HT1 has been identified, a trigger signal $S_{Tr}$ is sent to the CT system 70. If, by contrast, a noise alert has been received, no trigger signal $S_{Tr}$ is sent, so the CT system 70 is not erroneously synchronized with noise.

Figure 6:
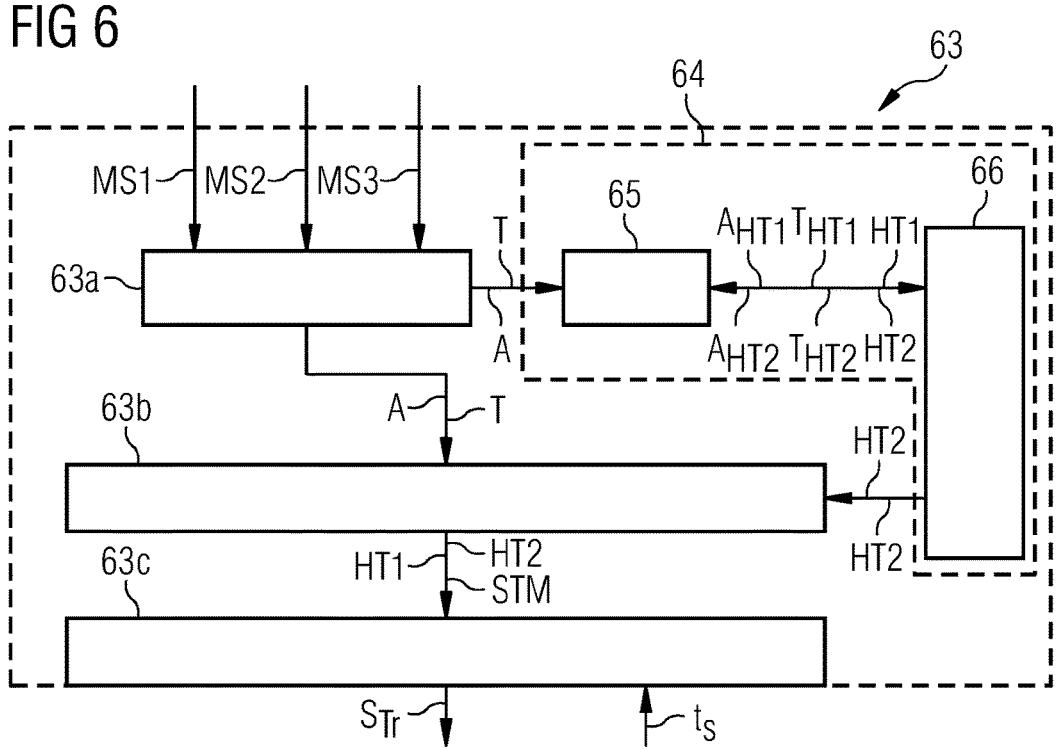
FIG. 6 depicts a schematic representation of a differential measuring system according to an exemplary embodiment.

FIG. 6 illustrates in detail the noise detection device 63 that was sketched in FIG. 5. In addition to the units 63a, 63b, 63c described above, the noise detection unit 63 also includes a learning procedure unit 64 (marked in dashed lines). Before the actual heart investigation, the learning procedure unit 64 serves to carry out a learning procedure in which individual heartbeat types HT1, HT2 of the patient P to be investigated are detected and stored. The learning procedure unit includes a heartbeat type identification unit 65 which is intended to identify a heartbeat type HT1, HT2 on the basis of characteristic features A, T of a measured signal MS1, MS2, MS3 that have been detected by the multi-channel feature recognition unit 63a. For this purpose, the detected features A, T of the measured signals MS1, MS2, MS3 are compared with characteristic features $A_{HT1}$, $T_{HT1}$ $A_{HT2}$, $T_{HT2}$ of heartbeat types HT1, HT2 that have already been detected and stored. For this, the corresponding feature data $A_{HT1}$, $T_{HT1}$ $A_{HT2}$, $T_{HT2}$ is retrieved from a memory unit 66 and compared with the features A, T that are currently being identified of the measured signals MS1, MS2, MS3 of the individual channels K1, K2, K3. If the identified features A, T do not agree with one of the already known heartbeat types HT1, HT2 or the characteristic features $A_{HT1}$, $T_{HT1}$ $A_{HT2}$, $T_{HT2}$ thereof, a new heartbeat type with the corresponding characteristic features is stored in the memory unit 66. Otherwise, no new heartbeat type is defined. During the actual heart investigation, the identified heartbeat types HT1, HT2 undergo a query by the heartbeat checking unit 63b, to identify whether characteristic features A, T of measured signals MS1, MS2, MS3 are to be associated with a heartbeat type HT1, HT2 or whether the detected measured signals MS1, MS2, MS3 are noise.

Finally, it may be pointed out once more that the devices and methods that have been described in detail above are merely exemplary embodiments, which those skilled in the art will be able to modify in a most diverse variety of ways without departing from the scope of the disclosure. Furthermore, the use of the indefinite articles "a" and "an" does not exclude the possibility that a plurality of the features concerned may also be present. Nor is the possibility excluded that elements of the present disclosure that are represented as individual units may include a plurality of cooperating part components that may also where appropriate be spatially distributed.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for detecting noise signals of a differential voltage measuring system for measuring cardiac movements in a patient, the method comprising:
   contacting the patient with at least two measuring electrodes having at least one associated measuring channel;
   performing a learning procedure comprising detecting learning signals from the patient over the at least one measuring channel, identifying at least one heartbeat type based on the detected learning signals, and storing the at least one heartbeat type;
   performing a heartbeat measurement following the performing of the learning procedure;
   detecting, during the heartbeat measurement, signals from the patient over the at least one measuring channel; and
   checking whether a detected signal of the detected signals from the heartbeat measurement has been caused by noise by comparing the detected signal with the at least one stored heartbeat type identified in a course of the learning procedure, wherein the detected signal is classified as noise when the detected signal does not correspond to any stored heartbeat type of the at least one stored heartbeat type.

2. The method of claim 1, wherein contact is made with the patient by three measuring electrodes, and the signals from the patient are detected over at least two measuring channels.

3. The method of claim 1, wherein, during the learning procedure, characteristic features are identified during the identification of the heartbeat type based on the detected learning signals, and the at least one heartbeat type is stored together with the characteristic features associated therewith.

4. The method of claim 3, wherein the characteristic features comprise at least one of the following variables:
   amplitude of a heartbeat,
   duration of the heartbeat, or
   a relationship between amplitudes of the detected learning signals of different measuring channels.

5. The method of claim 4, wherein, during the learning procedure, when characteristic features occur for a first time, the method further comprises:
   defining a new heartbeat type based on the characteristic features; and
   storing the new heartbeat type with the characteristic features,
   wherein subsequent signals having similar characteristic features are associated with the stored new heartbeat type.

6. The method of claim 1, wherein a first heartbeat type is stored for an underlying heartbeat of the patient and, in a case of arrhythmia, further heartbeat types are stored that have characteristic features differing from the first heartbeat type.

7. The method of claim 1, wherein a source of noise is connected up when the heartbeat is measured.

8. The method of claim 7, wherein the source of noise is a radiation source with ionizing radiation.

9. The method of claim 1, wherein the detected signal of the detected signals from the heartbeat measurement is identified as an underlying signal when the detected signal is associated with a stored heartbeat type of the at least one stored heartbeat type.

10. The method of claim 9, wherein, when the detected signal of the detected signals from the heartbeat measurement is identified as an underlying signal, the detected signal is used as a trigger signal for an irradiation procedure.

11. The method of claim 1, further comprising:
    measuring properties of the boundary between a measuring electrode and skin of the patient during the heartbeat measurement,
    wherein the noise is identified in dependence on measured values of the properties of the boundary between the measuring electrode and the skin.

12. A differential voltage measuring system comprising:
    at least two measuring electrodes;
    a memory;
    a measuring device having:
       at least one measuring channel configured to detect learning signals of the at least two measuring electrodes in a learning procedure, wherein at least one heartbeat type is configured to be identified based on the detected learning signals, wherein the at least one heartbeat type is configured to be stored in the memory; and a noise detection device comprising an input interface configured to detect signals from a patient over at least one measuring channel in contact with the patient by way of two measuring electrodes, and a heartbeat checking unit configured to check whether a detected signal has been caused by noise by comparing the detected signal with the at least one heartbeat type identified in a course of the learning procedure, wherein the detected signal is classified as noise when the detected signal does not correspond to any stored heartbeat type of the at least one stored heartbeat type.

13. A differential voltage measuring system having a computer program configured to be loaded directly to a memory device of the differential voltage measuring system, the computer program having program sections configured to, when the program is run in the differential voltage measuring system, cause the differential voltage measuring system to:

perform a learning procedure comprising detecting learning signals from a patient over the at least one measuring channel, identifying at least one heartbeat type based on the detected learning signals, and storing the at least one heartbeat type;

perform a heartbeat measurement of the patient following the performing of the learning procedure;

detect signals from the patient over at least one measuring channel during the heartbeat measurement; and check whether a detected signal of the detected signals from the heartbeat measurement has been caused by noise by comparing the detected signal with the at least one stored heartbeat type identified in a course of the learning procedure, wherein the detected signal is classified as noise when the detected signal does not correspond to any stored heartbeat type of the at least one stored heartbeat type.

* * * * *